United States Patent
Stievater et al.

(10) Patent No.: US 10,054,546 B2
(45) Date of Patent: Aug. 21, 2018

(54) WAVEGUIDE-ENHANCED RAMAN SCATTERING SPECTROSCOPY OF ANALYTES USING SORBENTS

(71) Applicant: THE UNITED STATES OF AMERICA, AS REPRESENTED BY THE SECRETARY OF THE NAVY, Washington, DC (US)

(72) Inventors: Todd H. Stievater, Arlington, VA (US); Jacob B. Khurgin, Pikesville, MD (US); Dmitry A. Kozak, Berwyn Heights, MD (US); Scott A. Holmstrom, Tulsa, OK (US); R. Andrew McGill, Lorton, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 238 days.

(21) Appl. No.: 15/293,394

(22) Filed: Oct. 14, 2016

(65) Prior Publication Data

US 2017/0108439 A1  Apr. 20, 2017

Related U.S. Application Data

(60) Provisional application No. 62/241,816, filed on Oct. 15, 2015.

(51) Int. Cl.
*G01J 3/44* (2006.01)
*G01N 21/65* (2006.01)
(Continued)

(52) U.S. Cl.
CPC ........... *G01N 21/658* (2013.01); *G02B 6/124* (2013.01); *G01N 2021/651* (2013.01); *G01N 2021/773* (2013.01); *G02B 21/02* (2013.01)

(58) Field of Classification Search
CPC ....... G01N 2021/651; G01N 2021/773; G01N 21/658; G02B 21/02; G02B 6/124
(Continued)

(56) References Cited

U.S. PATENT DOCUMENTS

| 6,579,722 B1* | 6/2003 | Collins | ............... G01N 21/766 436/172 |
| 9,599,567 B2* | 3/2017 | McGill | ................. G01N 30/74 |

(Continued)

OTHER PUBLICATIONS

Dhakal, Ashim et al., Evanescent Excitation and Collection of Spontaneous Raman Spectra Using Silica Nitride Nanophotonic Waveguides, Optics Letters, Jul. 1, 2014, pp. 4025-4028, vol. 39, No. 13, Optical Society of America, Washington, DC, USA.

(Continued)

*Primary Examiner* — Sunghee Y Gray
(74) *Attorney, Agent, or Firm* — US Naval Research Laboratory; Suresh Koshy

(57) ABSTRACT

A system and method for detecting an analyte includes a waveguide configured to receive a narrow-band laser signal; and a sorbent material covering an analyte detection region of the waveguide, wherein the sorbent material is configured to sorb the analyte and bring the analyte to an evanescent field of the waveguide, and wherein Raman scattering is produced by an interaction of the evanescent field and the analyte sorbed in the sorbent material along the analyte detection region of the waveguide, and the waveguide is further configured to collect the Raman scattering along the analyte detection region of the waveguide, wherein the collected Raman scattering indicates a type of the analyte.

10 Claims, 12 Drawing Sheets

(51) Int. Cl.
*G02B 6/124* (2006.01)
*G02B 21/02* (2006.01)
*G01N 21/77* (2006.01)

(58) Field of Classification Search
USPC .......................................................... 356/301
See application file for complete search history.

(56) References Cited

U.S. PATENT DOCUMENTS

| | | | | |
|---|---|---|---|---|
| 2004/0142484 | A1* | 7/2004 | Berlin | G01N 21/65 436/171 |
| 2011/0271738 | A1* | 11/2011 | McGill | G01N 21/64 73/23.41 |
| 2014/0260535 | A1* | 9/2014 | McGill | G01N 30/74 73/23.37 |

OTHER PUBLICATIONS

Chrimes, Adam et al., Microfluidics and Raman Spectroscopy: Current Applications and Future Challenges, Chem. Soc. Rev., Apr. 26, 2013, pp. 5880-5906, vol. 42. Royal Society of Chemistry, London, UK.

Hanf, Stefan et al., Fiber-enhanced Raman Multigas Spectroscopy: A Versatile Tool for Environmental Gas Sensing and Breath Analysis, Analytical Chemistry, May 20, 2014, pp. 5278-5285, vol. 86, American Chemical Society, Washington, DC, USA.

Li, Xiaoyun et al., Near-confocal Cavity-enhanced Raman Spectroscopy for Multitrace-gas Detection, Optics Letters, Sep. 15, 2008, pp. 2143-2145, vol. 33, No. 18, Optical Society of America, Washington, DC., USA.

Kozak, Dmitry et al., Infrared Spectroscopy for Chemical Agent Detection Using Tailored Hypersorbent Materials, Next Generation Spectroscopic Technologies VII, Proc. of SPIE, 2015, pp. 94280E-1-94280E-9, vol. 94280, SPIE, Bellingham, Washington, USA.

Stievater, Todd et al., Trace Gas Absorption Spectroscopy Using Functionalized Microring Resonators, Optics Letters, Feb. 11, 2014, pp. 969-972, vol. 39, No. 4, Optical Society of America, Washington, DC., USA.

Higgins, Bernadette et al., Synthesis and Characterization of Hyperbranched Hydrogen Bond Acidic Carbosilane Sorbent Polymer, Journal of Polymer Science: Part A: Polymer Chemistry, 2010, pp. 3000-3009, vol. 48, Wiley Periodicals, Inc., Hoboken, NJ, USA.

Subramanian, Ananth et al., Silicon and Silicon Nitride Photonic Circuits for Spectroscopic Sensing On-a-chip, Photon. Rev., Oct. 2015, pp. B47-B59, vol. 3, No. 5, Chinese Laser Press, Shanghai, China.

Dhakal, Ashim et al., Efficiency of Evanescent Excitation and Collection of Spontaneous Raman Scattering Near High Index Contrast Channel Waveguides, Optics Express, Oct. 9, 2015. pp. 27391-27404, vol. 23, No. 21. Optical Society of America, Washington, DC., USA.

* cited by examiner

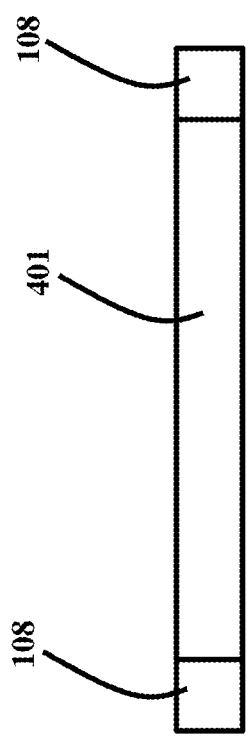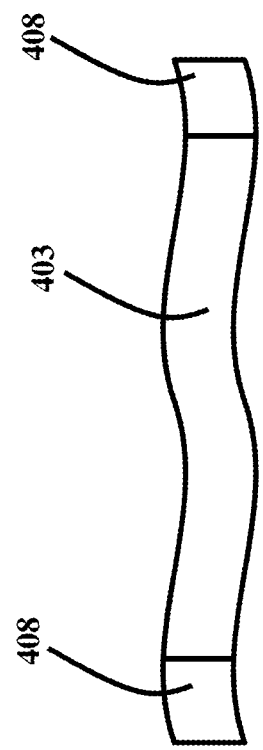
FIG. 4A
FIG. 4B

WAVEGUIDE-ENHANCED RAMAN SCATTERING SPECTROSCOPY OF ANALYTES USING SORBENTS

CROSS-REFERENCE TO RELATED APPLICATIONS

This application claims priority to U.S. Provisional Patent Application No. 62/241,816 filed on Oct. 15, 2015, the complete disclosure of which, in its entirety, is herein incorporated by reference.

GOVERNMENT INTEREST

The embodiments described herein may be manufactured, used, and/or licensed by or for the United States Government without the payment of royalties thereon.

BACKGROUND

Technical Field

The embodiments herein generally relate to chemical detection systems, and more particularly to optical techniques used for detecting chemicals.

Description of the Related Art

Benchtop Raman spectrometers are analytical tools for the detection or identification of unknown solids and liquids. The extension of this technology to handheld systems for trace concentrations of vapor-phase chemicals is extremely important for applications ranging from breath analysis to environmental monitoring to chemical warfare agent detection. The miniaturization of gas-phase detection systems is hindered by the extremely weak Raman signal generated from a dilute vapor over short interaction lengths. Recent improvements towards this end have used resonant cavities or multipass cells that are tens of centimeters long, but these designs are not likely to be implemented in an inexpensive, handheld platform. An enhancement of Raman signals from multicomponent vapors using hollow-core optical fibers have shown part-per-million (ppm) detection limits, but these systems suffer from cumbersome techniques for removing analytes from the fiber after exposure.

SUMMARY

In view of the foregoing, an embodiment herein provides a system for detecting an analyte, the system comprising a waveguide configured to receive a narrow-band laser signal; and a sorbent material covering an analyte detection region of the waveguide, wherein the sorbent material is configured to sorb the analyte and bring the analyte to an evanescent field of the waveguide, and wherein Raman scattering is produced by an interaction of the evanescent field and the analyte sorbed in the sorbent material along the analyte detection region of the waveguide, and the waveguide is further configured to collect the Raman scattering along the analyte detection region of the waveguide, wherein the collected Raman scattering indicates a type of the analyte.

The Raman scattering may comprise back-scattered Raman scattering, and the system may further comprise an optical detector configured to detect the back-scattered Raman scattering, which indicates the type of the analyte and propagates in an opposite direction as the narrow-band laser signal. The Raman scattering may comprise forward-scattered Raman scattering, and the system may further comprise an optical detector configured to detect forward-scattered Raman scattering, which indicates the type of the analyte and propagates in a same direction as the narrow-band laser signal.

The system may further comprise a pump laser source configured to generate a laser signal, the laser signal comprising the narrow-band laser signal; a band pass filter placed between the pump laser source and the waveguide, wherein the band pass filter is configured to filter the laser signal at frequencies of the narrow-band signal; an optic configured to focus the narrow-band signal on a first coupling component of the waveguide; and a flow cell, wherein the waveguide may be located inside the flow cell, and wherein the flow cell may comprise a passage configured to allow a gas flow through the flow cell; and a first window and a second window, wherein the first and second windows are configured to allow light in and out of the flow cell.

The system may further comprise a reflecting microscope objective that uses a Schwarzschild reflective objective, and may be configured to collect the Raman scattering transmitted by a second coupling component of the waveguide through the second window; and reduce chromatic dispersion in the collection of Raman scattering; and an off-axis parabolic mirror configured to couple the Raman scattering to the optical detector. The optical detector may comprise any of a 300-groove/mm, 1.3 µm-blaze grating and a liquid nitrogen cooled, 1024 element InGaAs linear array detector, and a spectrograph configured to identify the analyte using wavelengths of the Raman scattering.

The system may further comprise a long-pass edge filter placed between the waveguide and the optical detector, wherein the long-pass edge filter may be configured to block the narrow-band signal from the optical detector. The laser signal may comprise any of 513 nm, 532 nm, 633 nm, 785 nm, 830 nm, 850 nm, and 980 nm wavelengths. The laser signal may comprise any of a predominantly in-plane (quasi-transverse electric) polarization and an out-of-plane (quasi-transverse magnetic) polarization.

The system may further comprise a detection device comprising a substrate layer comprising a substrate material; a bottom cladding layer comprising a bottom cladding material, wherein the bottom cladding layer covers the substrate layer; and a core layer comprising a core material, wherein the core layer covers the bottom cladding layer, wherein the core material has a refractive index higher than the bottom cladding material, wherein the waveguide is patterned in the core layer, and wherein the bottom cladding material and the core material are transparent at frequencies of the narrow-band signal and the Raman scattering frequencies. The substrate material may comprise silicon, the bottom cladding material may comprise silicon oxide, and the core material may comprise silicon nitride.

Another embodiment herein provides a device configured to detect an analyte, wherein the device comprises a substrate layer comprising a substrate material; a bottom cladding layer comprising a bottom cladding material, wherein the bottom cladding layer covers the substrate layer; a core layer comprising a core material, wherein the core layer covers the bottom cladding layer, wherein the core layer material has a refractive index higher than the bottom cladding material, and wherein a waveguide is patterned in the core layer; and a sorbent coating covering an analyte detection region of the waveguide, wherein the sorbent coating is configured to: increase a density of analyte molecules inside the sorbent coating compared to an ambient environment above the sorbent coating; and bring the analyte to an evanescent field of the waveguide, and wherein Raman scattering, produced by an interaction of the evanescent field and the analyte sorbed in the sorbent coating, is collected by the waveguide along the analyte detection region and indicates a type of the analyte.

The substrate material may comprise silicon, the bottom cladding material may comprise silicon oxide, the core material may comprise silicon nitride, and the sorbent coating may comprise hydrogen-bond acidic hyperbranched carbosilane fluoroalcohol. The device and a pump laser source may be integrated on a single photonic integrated circuit, and wherein the pump laser source may be configured to generate a laser radiation and couple the laser radiation to the waveguide.

The Raman scattering may comprise forward-scattered Raman scattering which travels in a same direction as the laser radiation, wherein the device may further be integrated on the photonic integrated circuit with any of a band pass filter placed between the pump laser source and the waveguide, wherein the band pass filter is configured to filter the laser radiation at narrow-band frequencies; an optical detector configured to detect the forward-scattered Raman scattering indicating the type of the analyte; and a long-pass edge filter placed between the waveguide and the optical detector, wherein the long-pass edge filter is configured to block the laser radiation from the optical detector.

The device may further be integrated on the photonic integrated circuit with an optical detector configured to detect back-scattered Raman scattering, and wherein the back-scattered Raman scattering may indicate the type of the analyte and propagates in an opposite direction as the laser radiation.

Another embodiment herein provides a method for detecting an analyte, wherein the method comprises providing a device comprising a substrate layer, a bottom cladding layer covering the substrate layer, a core layer covering the bottom cladding layer and comprising a waveguide, and a sorbent coating covering the waveguide; exposing the sorbent coating to the analyte; inputting a laser signal to the waveguide; and detecting the analyte using a Raman scattering produced by an interaction of the laser signal with the analyte in the sorbent coating.

The sorbent coating may be configured to increase a density of analyte molecules inside the sorbent coating compared to an ambient environment above the sorbent coating. The substrate layer may comprise silicon, the bottom cladding layer may comprise silicon oxide, the core layer may comprise silicon nitride, and the sorbent coating may comprise hydrogen-bond acidic hyperbranched carbosilane fluoroalcohol. The core layer may be deposited over the bottom cladding layer and may be configured to allow for low-loss light propagation at near-infrared wavelengths in the waveguide etched in the core layer.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 4A is a schematic diagram illustrating a waveguide according to an embodiment herein;

FIG. 4B is a schematic diagram illustrating a waveguide according to another embodiment herein;

DETAILED DESCRIPTION

Figure 1:
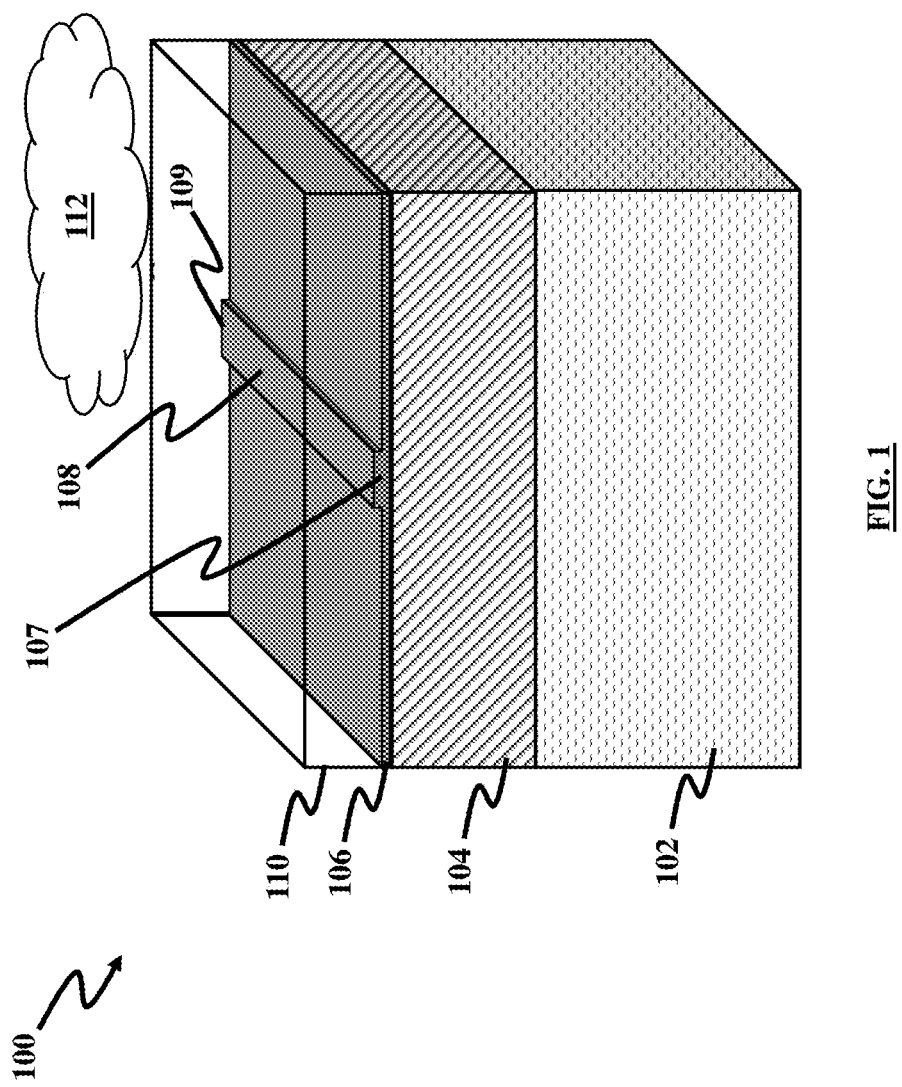
FIG. 1 is a schematic diagram of a device according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Bulk solid phase extraction media may be used to reversibly concentrate organic contaminants in water and air prior to spectral characterization by Raman scattering. Liquid-phase Raman signal enhancement by an evanescent waveguide may be used by placing the liquid analyte in direct contact with the waveguide core. Systems used for Raman spectroscopy of liquids on a chip using microfluidics with waveguides to confine the Raman excitation and signal may not co-propagate the pump and signal for waveguide-enhanced Raman scattering.

It is desirable to provide a handheld device that is capable of trace gas analyte identification. Embodiments herein provide coating a highly evanescent optical waveguide with a hypersorbent polymer. These waveguides may permit the reversible detection of Raman spectra at parts-per-billion (ppb) analyte concentrations in waveguide lengths less than approximately 1 cm.

This detection limit in such a short optical interaction length is made possible by the embodiments herein for a number of reasons. First, the density of target analyte molecules may increase inside the hypersorbent polymer by a factor of as much as approximately $10^8$ compared to the ambient environment above the sample. Second, a significant fraction of the guided-mode power of the coated waveguide evanescently overlaps with the hypersorbent polymer cladding. Third, a pump continuously generates Raman scattering all along the length of the waveguide as it propagates. Fourth, the scattered signal is efficiently collected by propagating modes of the waveguide and guided to the end where it can be easily collected for detection.

The embodiments herein provide using a naturally reversible hypersorbent polymer such that when the concentration of target vapors in the surrounding air changes, the enhanced concentration in the polymer follows.

By using functionalized waveguides for enhanced Raman scattering, the embodiments herein provide inexpensive integrated photonic integrated circuit (PIC) architectures that may include the source and detector on the same chip. In addition, in the embodiments herein, multiple hypersorbent coatings may be used on the same chip to enable sensing of multiple classes of chemicals, such as hydrocarbons, toxic industrial chemicals, or organophosphonates.

In the embodiments herein, sorbent polymers may be designed to target molecular interactions with a variety of hazardous chemicals including explosives, chemical agents, narcotics, and toxic industrial chemicals. Applications of functionalized sorbent polymers may include preconcentrator devices, solid phase microextraction (SPME) fibers, membrane introduction systems, chromatographic stationary phases and coatings for chemical sensors. The ratio of the analyte concentration in the sorbent to that in the ambient environment outside the sorbent is defined at the partition coefficient. Sorbents with an ultra-high partition coefficient are referred to as hypersorbents. Some embodiments herein use HCSFA2 hypersorbent, which is a hydrogen-bond acidic hyperbranched carbosilane uoroalcohol designed to target hydrogen-bond basic hazardous chemicals such as chemical warfare agents and organophosphonates.

Photonic integrated circuits (PICs) are planar lightwave waveguides and components that are combined together on a single chip, in analogy with electronic integrated circuits (ICs). Similar to electronic ICs, PICs benefit from the manufacturing scalability provided in semiconductor integration. These benefits include cost, standardization, size, weight, and power management. In some embodiments herein, the subwavelength feature sizes and high-index confinement offer optical advantages and functionality that are not possible in larger, bulk devices.

Spectroscopic optical sensors fabricated from PICs have so far been a poor match for chemical sensing applications, since spectral regions at which most chemicals have their fingerprints (the mid-wave and long-wave IR) are outside of the range of PICs. Molecular overtones do fall within the PIC spectrum in the near-infrared (NIR), but the interaction lengths are typically much longer than the size of the PIC since the overtone absorption is so weak. Raman spectroscopy with sorbent materials, as provided by the embodiments herein, is attractive for PIC platforms because it falls within the NIR, and is still sensitive enough within the short interaction length of a PIC.

Referring now to the drawings, and more particularly to FIGS. 1 through 11, where similar reference characters denote corresponding features consistently throughout the figures, there are shown preferred embodiments.

FIG. 1 is a schematic diagram illustrating a device 100 for Raman spectroscopy of a trace gas 112 according to an embodiment herein. In an embodiment, the device 100 includes a stacked configuration including a first layer 102, a second layer 104 covering the first layer 102, and a third layer 106 covering the second layer 104. In an embodiment, the third layer 106 has a refractive index higher than the second layer 104. The third layer 106 may be patterned to include the waveguide 108. In an embodiment, the third layer 106 is etched to include a rib waveguide 108 including facets 107, 109. In an embodiment, the first layer 102 is a substrate layer, the second layer 104 is a bottom cladding layer, and the third layer 106 is a core layer.

In an embodiment, the device 100 includes a sorbent layer (or coating) 110 that covers the waveguide 108. In an exemplary embodiment, the first layer 102 includes silicon (Si), the second layer 104 includes silicon oxide ($SiO_2$), the third layer 106 includes silicon nitride (SiN), and the sorbent coating 110 includes hypersorbent material.

In an exemplary embodiment, the chip-scale rib waveguide 108 includes an approximately 175 nm thick SiN layer 106 deposited by low-pressure chemical vapor deposition (LPCVD) over the $SiO_2$ layer 104. Low-pressure chemical vapor deposition of SiN allows for low-loss light propagation at near-infrared wavelengths. In an exemplary embodiment, the $SiO_2$ layer 104 is an approximately 5 μm thick thermal $SiO_2$ layer on the Si wafer 102. The thickness of the sorbent coating 110 may be non-uniform along the waveguide 108, and may be in the approximately 1-2 μm thickness range.

In the embodiments herein, instead of a straight rib waveguide 108, spirals, curves, microring resonators, or Fabry-Perot cavities may be used. In an embodiment, components for efficient coupling with the waveguide 108, such as gratings or tapers, may be used. In an embodiment, an oxide or other top claddings may be placed on top of the waveguide 108 in regions not coated with the sorbent coating 110 to protect the waveguide 108 from the environment.

In the embodiments herein, waveguides with different lengths or any cross-sections may be used. Either quasi transverse electric (TE) or quasi transverse magnetic (TM) waveguide modes can be used. Wider or thicker-core waveguides may enable a stronger signal by offering lower loss and pushing less electromagnetic field into the bottom $SiO_2$ layer 104. On the other hand, narrower waveguides may be used to enable more signal collection into the fundamental mode, and to push more mode into the sorbent coating 110. In the embodiments herein, waveguide 108 may be either single-mode or multi-mode. In an embodiment, waveguide 108 may be a partially etched rib waveguide, or a fully etched ridge waveguide. In another embodiment, the waveguide 108 may be etched to have a gap in the middle (i.e., a so-called "nanoslot waveguide") to increase the modal overlap with the sorbent 110. In an embodiment, waveguide 108 may use a sorbent material as its core.

In some embodiments, instead of a polymer sorbent material, any top cladding that brings analytes to the evanescent field of the waveguide may be used as the layer 110. This may include antibodies or proteins for biosensing, porous materials, liquids, metal-oxide materials for reactive chemistries, and non-sorbent polymers.

Figure 2:
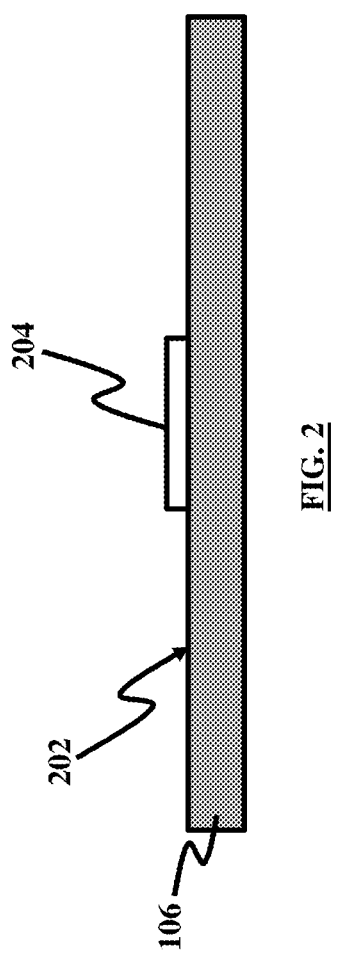
FIG. 2 is a schematic diagram illustrating an etching process for making a waveguide according to the embodiments herein.

FIG. 2, with reference to FIG. 1, is a schematic diagram illustrating etching the SiN layer 106 to create the rib waveguide 108, according to an embodiment herein. The surface 202 of the SiN layer 106 is patterned with a thin-film resist layer 204. The rib waveguide 108 is then created by etching the uncovered portion of the surface 202. In an embodiment, the etching comprises a 100 nm-deep reactive ion etch (RIE) process. In an example embodiment, the rib waveguide 204 is approximately 2 μm-wide.

In an embodiment, the wafer including the Si layer 102, SiO$_2$ layer 104, and SiN layer 106 is laser-scribed and cleaved along a silicon crystal plane to produce smooth ends on the waveguide 108 (facets 107 and 109) without the need for additional polishing. In an embodiment, the device 100 is cleaned using oxygen plasma ashing and a piranha rinse.

Figure 3:
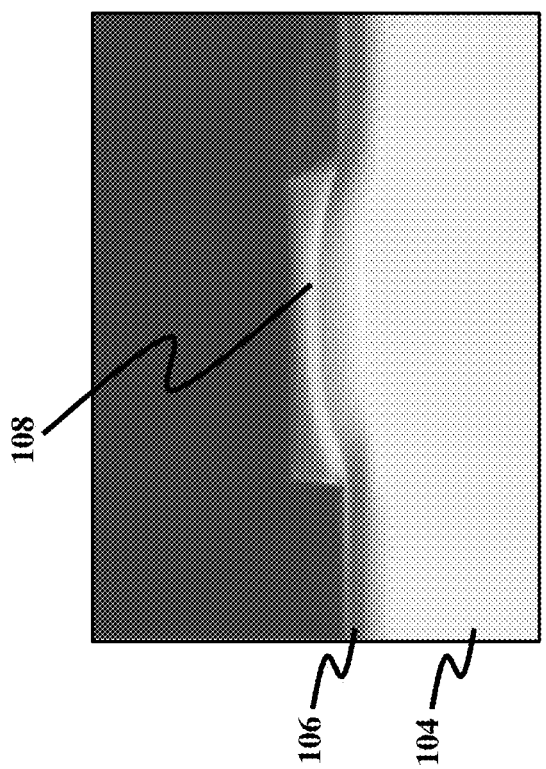
FIG. 3 is a microscopic image illustrating a waveguide according to the embodiments herein.

FIG. 3, with reference to FIGS. 1 and 2, is a microscopic image illustrating the SiO$_2$ layer 104, the SiN layer 106, and the rib waveguide 108 according to an embodiment herein.

FIG. 4A, with reference to FIGS. 1 through 3, is a schematic diagram illustrating the waveguide 108 with an analyte detection region 401, according to an embodiment herein. In an embodiment, only the analyte detection region 401 of the waveguide 108 is covered by the sorbent coating 110. In the analyte detection region 401, the evanescent field of the waveguide 108 continuously creates Raman scattering when it interacts with the analyte sorbed in the sorbent coating 110. A significant portion of the Raman scattering is then collected back into the waveguide 108. Therefore, the longer the waveguide 108, the more Raman scattering is detected. Therefore, it may be desirable to increase the length of the waveguide 108.

In some embodiments, different patterns for waveguide 108, for example spiral patterns, are used to increase the length of the waveguide 108. FIG. 4B, with reference to FIGS. 1 through 4A, is a schematic diagram illustrating a waveguide 408 with a curved pattern for increasing the length of the analyte detection region 403, according to an embodiment herein.

Figure 4C:
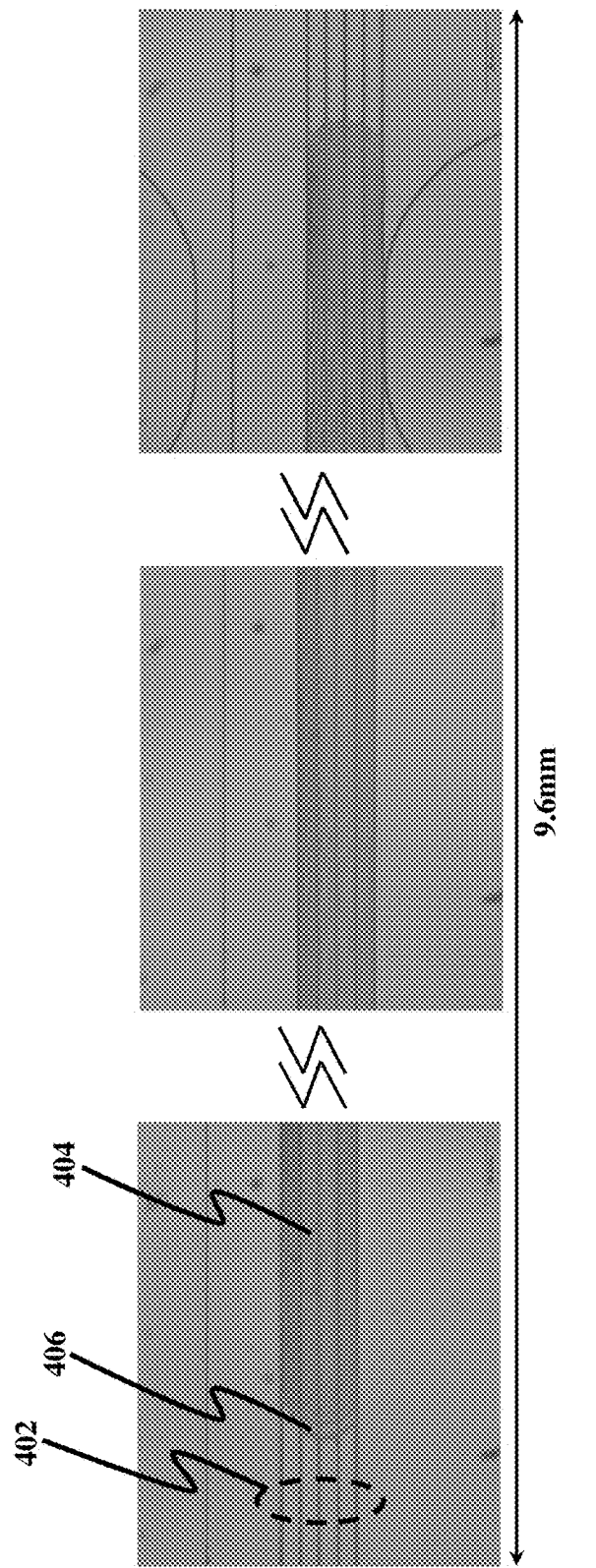
FIG. 4C is a microscopic image illustrating waveguides according to the embodiments herein.

In an embodiment, the Raman spectroscopy device 100 may include multiple waveguides. FIG. 4C, with reference to FIGS. 1 through 4B, is a microscopic image illustrating an approximately 9.6 mm-long cleaved sample including five rib waveguides 402 (the set of five horizontal dark lines). In an embodiment, each of the rib waveguides 402 are approximately 2 μm-wide. Shaded area 404 with interference fringes 406 is coated by the sorbent coating 110. The fringes 406 show non-uniformity of the sorbent coating 110, according to an embodiment herein. Non-uniformity of the sorbent coating 110 demonstrates the robustness of the device 100, and that it can work with a range of thicknesses of the sorbent coating 110, for example in the approximately 1-2 μm thickness range. In an exemplary embodiment, the analyte detection region of the waveguide 108 (or waveguides 402) is more than 98% of the length of the waveguide, and is coated with sorbent coating 110.

Figure 5:
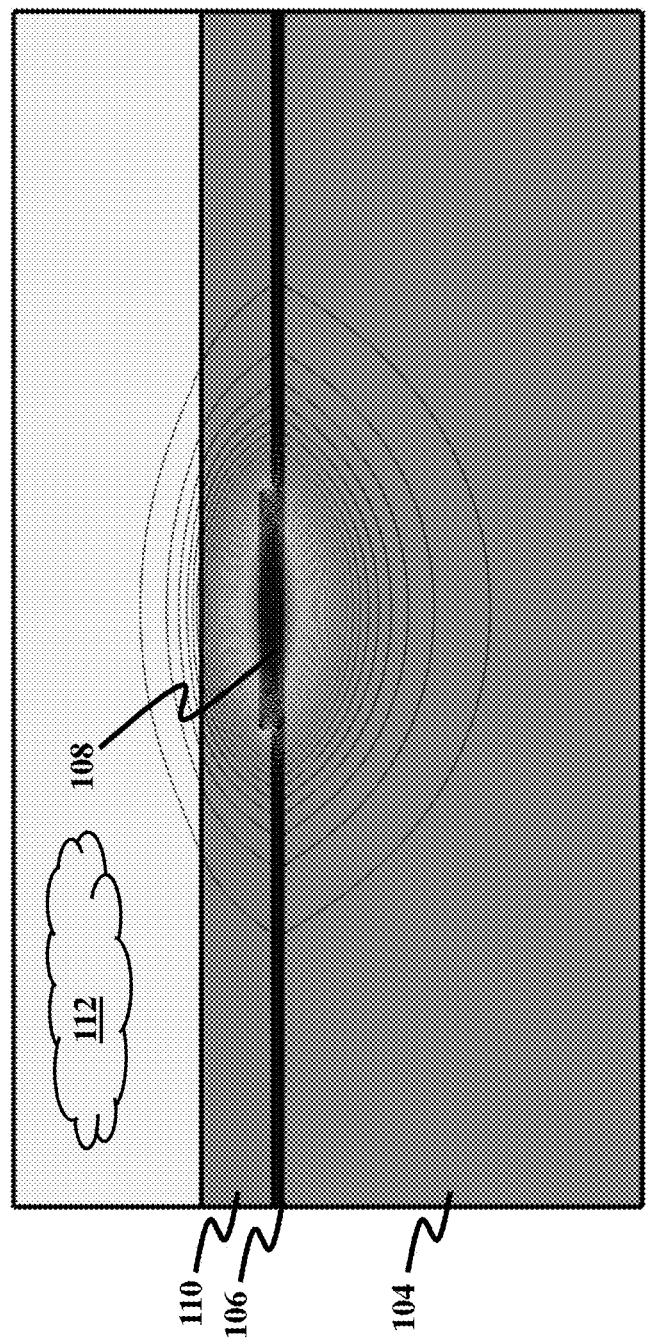
FIG. 5 is a schematic diagram illustrating electromagnetic fields within a waveguide according to the embodiments herein.

FIG. 5, with reference to FIGS. 1 through 4C, is a schematic diagram illustrating a finite element analysis of the horizontal component of the electric fields of the fundamental quasi TE mode, TE$_{00}$, for the waveguide 108 coated with the sorbent coating 110 according to an exemplary embodiment herein. The finite element analysis shows that approximately 25% of the modal power propagates within the sorbent coating 110, and would thus be capable of interacting with sorbed molecules of the trace gas 112.

Figure 6:
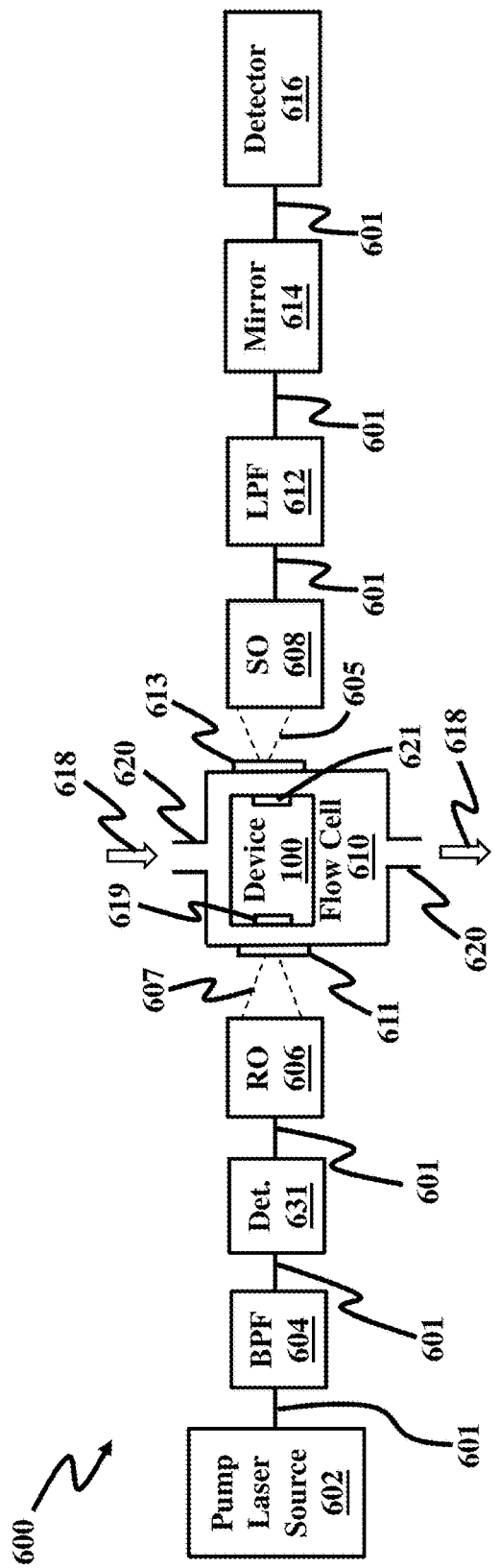
FIG. 6 is a schematic diagram illustrating a system according to an embodiment herein.

FIG. 6, with reference to FIGS. 1 through 5, is a schematic diagram illustrating a system 600 according to an embodiment herein. In an embodiment, the system 600 includes a pump laser source 602 configured to generate a laser signal. The pump laser source 602 may comprise an approximately 1.06 μm laser source. In an embodiment, the laser signal generated by the pump laser source 602 travels over the polarization-maintaining fibers (PMF) 601. In an exemplary embodiment, pump laser source 602 produces a polarized output of a 50 mW, 1064 nm, single longitudinal mode signal, using a Nd:YAG laser.

In an embodiment, the laser generated by the pump laser source 602 passes a band-pass filter (BPF) 604 configured to allow a narrow-band portion of the laser signal to pass through. The narrow optical bandpass filter 604 filters the signal at 1064 nm to minimize the amount of light entering the waveguide (e.g., waveguide 108) at other frequencies. After passing through the BPF 604, the narrow-band portion of the laser signal is focused by a refractive objective (RO) 606, as a signal 607, which may propagate through a flow cell window 611 and onto a first coupling component 619. The first coupling component 619 may be the facet 107 of the waveguide 108 in the device 100, or a grating coupler. In an exemplary embodiment, the RO 606 uses a 50× long-working-distance refracting microscope objective.

In an embodiment, the device 100 is mounted in the flow cell 610. In an embodiment, the flow cell 610 is a sealed, rectangular cuboid enclosure that may include glass windows 611, 613 on two sides, and tubing connectors 620 on two other sides that allow for the gas flow 618 perpendicular to the clear optical path through the system 600. In this regard, the flow cell 610 may include a passage 620 for gas flow 618 that includes the trace gas 112. The flow cell 610 may be purged continuously with nitrogen gas.

In an exemplary embodiment, when adding a chemical vapor as the trace gas 112, a separate line of nitrogen gas may be bubbled through a liquid chemical and the resulting analyte-saturated nitrogen may be combined with the continuously flowing nitrogen using a gas flow valve (not shown). Concentrations at the sample location may be controlled with gas flow controllers (not shown).

In exemplary embodiments, three analytes chosen in the trace gas 112 are ethyl acetate (EA), methyl salicylate (MeS), and dimethyl sulfoxide (DMSO) (which are listed in increasing order of partitioning into HCSFA2). These chemicals may be used for a couple of reasons. First, they are safe to use without extensive precautions for accidental exposure. Second, these molecules span a range of capacities for hydrogen bonding due to their structure; C=O for EA and MeS, and S=O for DMSO. As such, they serve as safe and appropriate surrogates for the toxic phophonate esters that have the capacity to form strong hydrogen bonds due to the P=O part of their chemical configuration.

The polarization of the signal 607 in the plane of the SiN layer 106 excites the fundamental quasi-TE mode, TE$_{00}$. As the pumped signal 607 propagates along the waveguide 108, a forward-scattered portion of the Raman scattering propagates in the same direction as the narrow-band laser signal and is captured by the waveguide 108. The forward-propagating Raman signal 605 exits a second coupling component 621, may pass through the opposite flow cell window 613, and is collimated with a reflecting microscope objective, using a Schwarzschild reflective objective (SO) 608. The second coupling component 621 may be the facet 109 of the waveguide 108 in the device 100, or a grating coupler. The reflecting objective 608 reduces chromatic dispersion in the light collection path. After passing through a long-pass edge filter (LPF) 612 to block the pumped signal 605, the remaining light is coupled, using an off-axis parabolic (OAP) mirror 614, into a detector 616. In an embodiment, the detector 610 is a 0.75 m spectrograph with a 300-groove/mm, 1.3 μm-blaze grating and a liquid nitrogen cooled, 1024 element InGaAs linear array detector. In an embodiment, each spectrum is collected for approximately 100 seconds. Post-collection processing may include stitching the multiple grating position spectra together and performing a five-point simple central moving average.

A back-scattered portion of the Raman scattering may travel back from the waveguide 108 in an opposite direction of the laser signal generated by the source 602. In an embodiment, a detector 631 is used to detect the back scattering signal. The detected back-scattering signal also indicates a type of analyte in the sorbent coating 110.

Fabry-Perot fringe analysis shows optical losses of approximately 2 dB/cm at wavelengths between 980 nm and 1600 nm for the excited waveguide mode. Functionalization of the waveguides 108 for trace gas detection may be achieved by coating the waveguide 108 with the hypersorbent polymer 110, HCSFA2, that becomes the upper cladding of the waveguide structure 108 in device 100. In an embodiment, the hypersorbent polymer 110 has two hexauoroisopropanol groups per repeat unit that facilitate hydrogen bonding with important gas phase analytes, such as phosphonate ester nerve agents or nitroaromatics, that have a large hydrogen-bond basicity. The hypersorbent polymer 110 may be deposited from a cyclohexanone solution onto the waveguide 108 (or waveguides 402) using a rastered microcapillary tip.

In an embodiment, Raman pump wavelengths such as 513 nm, 532 nm, 633 nm, 785 nm, 830 nm, 850 nm, or 980 nm may be used in the pump laser source 602. In the embodiments herein, the Raman signal that is either co-propagating or counter-propagating with the pump may be used. That is, the waveguide 108 samples may be used either in backward or forward scattering mode, or both. In the embodiments herein, both modes that are predominantly polarized in-plane (quasi-TE) or out-of-plane (quasi-TM) may be used, for either the pump or the signal.

Figure 7:
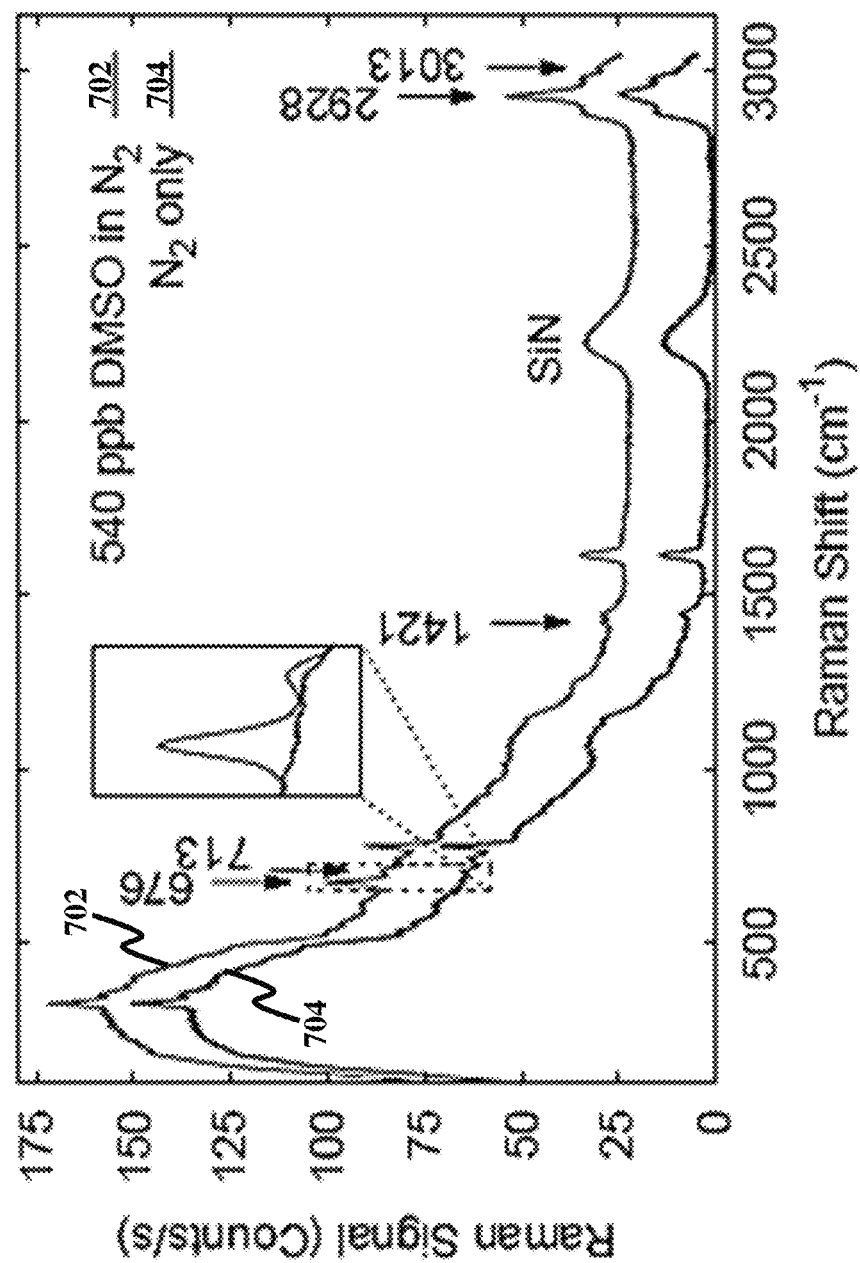
FIG. 7 is a graph illustrating Raman signal vs. Raman shift according to the embodiments herein.

FIG. 7, with reference to FIGS. 1 through 6, is a diagram illustrating a typical Raman scattering spectra. Line 704 illustrates Raman scattering spectra before exposure to 540 ppb DMSO, and line 702 illustrates Raman scattering during exposure to 540 ppb DMSO. The spectrum during exposure to DMSO (e.g., line 702) is shifted upwards for clarity. The sharp rise occurring at small Raman shifts is associated with the edge of the long pass filter 612. The broad feature below 1500 cm$^{-1}$ is attributed to a combination of fluorescence and Raman scattering. The 676 cm$^{-1}$ and 713 cm$^{-1}$ Raman shift markers in FIG. 7 indicate spectral features that are easily associated with sorbed-phase DMSO even in the raw spectrum.

Figure 8:
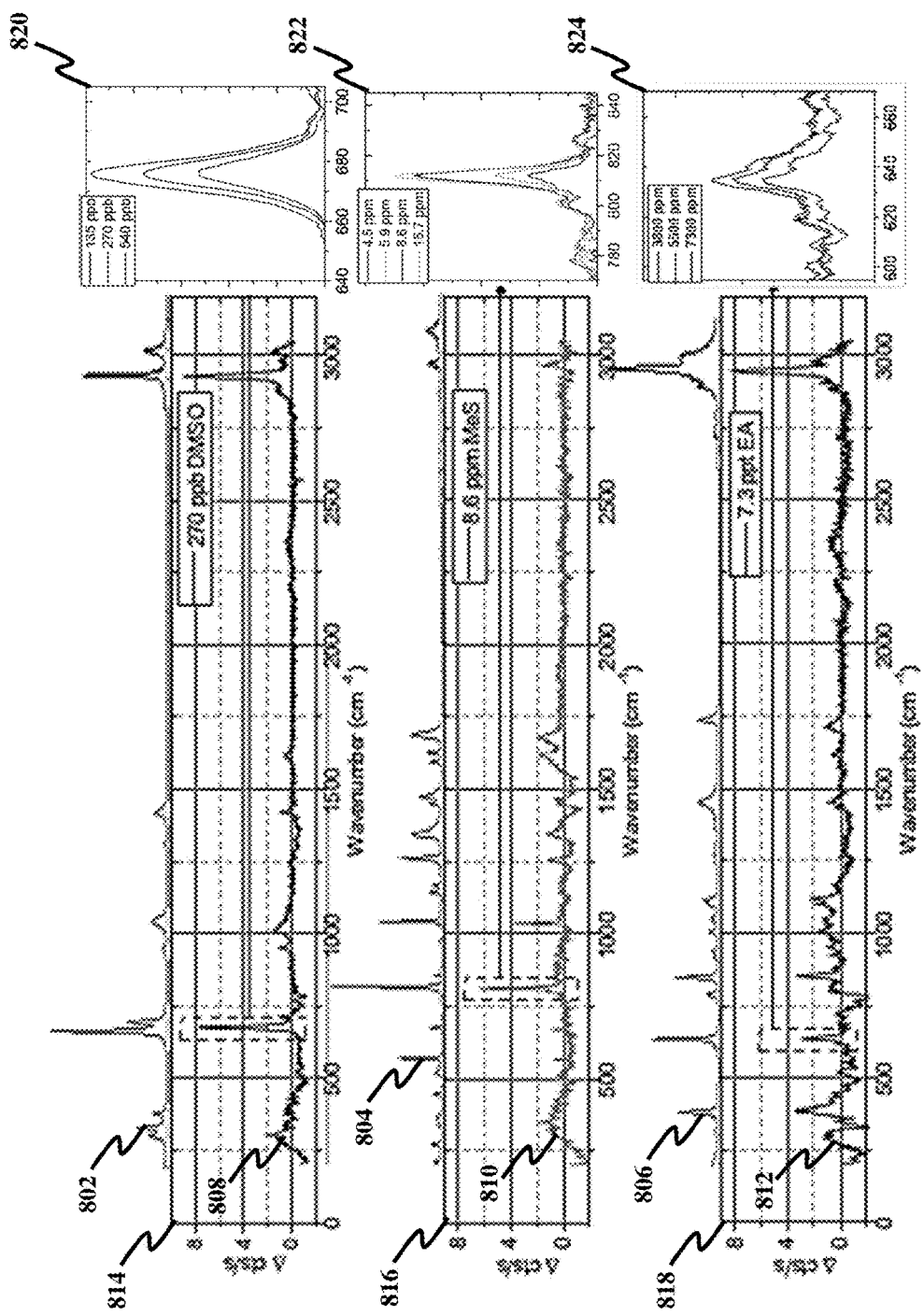
FIG. 8 are graphs illustrating Raman spectra before and during exposure of an analyte detecting device to three analytes according to the embodiments herein.

FIG. 8, with reference to FIGS. 1 through 7, are graphs illustrating the difference of Raman spectra before and during exposure of the device 100 to three analytes DMSO, MeS, and EA, according to embodiments herein. Graph 814 corresponds to exposure to 270 ppb DMSO, graph 816 corresponds to exposure to 8.6 ppm MeS, and graph 818 corresponds to exposure to 7.3 ppt (parts per trillion) EA.

The spectra before and after exposure are first normalized to help account for optical power throughput differences in the spectra. The resulting spectra are then subtracted resulting in raw difference spectra, but having a broadly undulating background. A polynomial is fit to the undulating background is subtracted from the raw difference spectra to obtain the spectra shown.

Measured difference Raman spectrum 808, 810, and 812 according to the embodiments herein are shown in FIG. 8, with liquid-phase Raman spectra 802, 804, and 806 above each of the measured difference Raman spectrums 808, 810, and 812. As shown in FIG. 8, there is good agreement between each of the observed sorbed-phase spectral lines 808, 810, 812 and known Raman lines 802, 804, and 806 for the liquid phase of the analyte. The central positions of the Raman lines identified in difference spectra for each analyte are shown in Table 1.

TABLE 1

| DMSO | | MeS | | EA | |
|---|---|---|---|---|---|
| Known | Measured | Known | Measured | Known | Measured |
| 309 | 303 | 555 | 564 | 381 | 384 |
| 670 | 676 | | 669 | 637 | 635 |
| 700 | 713 | 814 | 812 | 849 | 851 |
| 1045 | 1008 | 1037 | 1036 | | 1099 |
| 1420 | 1421 | 1256 | 1254 | 1117 | 1118 |
| 2913 | 2928 | 1341 | 1344 | 1738 | 1713 |
| 2997 | 3013 | 1620 | 1618 | 2943 | 2945 |
| | | 1681 | 1681 | | |
| | | 2963 | 2965 | | |

The differences in the measured versus known values are presumptively due to differences in the sorbed-versus liquid-phase Raman signals of the analyte. It is noted that the measured numbers for DMSO, the molecule forming the strongest hydrogen bonds within the polymer, are the most shifted from the literature values. The strength of the hydrogen bond in sorbents can strongly affect the value of the polymer's O—H stretch resonance. Results derived from the embodiments herein further suggest that individual sorbed-phase Raman lines of the most strongly-bonded analytes may differ from those of the published liquid spectra. A full database for sorbed-phase Raman may therefore be required for spectral fingerprinting. The observation of multiple signature lines observed for each analyte studied indicates the efficacy of this method for trace gas identification.

To the right of each difference spectrum in graphs 814, 816, and 816 in FIG. 8, the concentration dependence is shown in graphs 820, 822, and 824, respectively. This data is used to extrapolate the lowest concentration level that is detectable using the device 100. In an exemplary embodiment herein, the smallest concentration measured for DMSO is 135 ppb but, even at this small concentration, the Raman line at 676 cm$^{-1}$ is far above the noise level in the spectrum. Based on the measured concentration dependence, the one-sigma limit of detection (LOD) for DMSO is 7.6 ppb, for MeS is 360 ppb, and for EA is 600 ppm.

Raman scattering in the evanescent field of photonic waveguides is modified compared to the bulk by the presence of discrete propagating modes. A calculation of waveguide Raman scattering efficiency should thus account for both the modified scattering rate as well as the collection efficiency into the waveguide modes. For a waveguide short enough to neglect loss and that supports only the fundamental TE mode, the forward-scattering efficiency is calculated herein to be:

$$\eta = \frac{n_{HC}^2 \lambda_s \lambda_p \sigma L N_{HC}}{8\pi} \frac{n_g \iint_{HC} |E(x,y)|^4 dxdy}{(\iint_\infty n^2(x,y)|E(x,y)|^2 dxdy)^2} \quad (1)$$

where $\eta = P_s/P_p$, the internal conversion efficiency of pump to probe, $\lambda_s$ is the Raman signal wavelength, $\lambda_p = 1064$ nm, $\sigma$ is the Raman scattering cross-section, L is the waveguide length, $N_{HC}$ is the analyte number density in the HCSFA2 layer, $n_g$ is the group index, n is the material refractive index, $n_{HC}$, and $E(x, y)$ is the transverse electric field strength. The integral in the numerator is taken only over the HCSFA2 layer, whereas the integral in the denominator is over the whole waveguide. Assuming uniform sorption, the analyte number in a sorbent is given by $N_{HC}=KN_{vapor}$ where K is the partition coefficient for the particular analyte under investigation and $N_{vapor}$ is the vapor number density sent to the sample. For DMSO at 500 ppb, $N_{vapor}$ is $1.2 \times 10^{17}$ m$^{-3}$ and K~$1 \times 10^8$. Using the approximation $\sigma=1 \times 10^{-33}$ m$^2$/sr, and Comsol Multiphysics to calculate the field overlap integrals and the group index, an efficiency is calculated herein to be $\eta=4.4 \times 10^{-13}$. This is similar to a measured efficiency herein of $10 \times 10^{-13}$. However, there may be a large degree of uncertainty in this efficiency due to uncertainty about the exact Raman cross-sections and the exact partition coefficient for this analyte.

Calculations herein show that, neglecting insertion losses or collection efficiencies, waveguide-based Raman scattering is enhanced compared with the traditional micro-Raman (surface-normal) technique ($\eta_{\mu R}$) by:

$$\eta/\eta_{\mu R} = \frac{n_{HC}^2 \lambda_s^2 L}{8\pi t_{HC}} \frac{n_g \int\int_{HC} |E(x,y)|^4 dxdy}{(\int\int_{\infty} n^2(x,y)|E(x,y)|^2 dxdy)^2} \quad (2)$$

where $t_{HC}$ is the thickness of the HCSFA2 layer. The term on the right can be thought of a modal overlap factor divided by the effective area of the waveguide. This efficiency enhancement is 40 for the geometry associated with the embodiments therein, and will only improve further with longer, lower loss, narrower waveguides.

Similar to other hypersorbent polymers, it is expected that the P=O molecules have similar or larger partition coefficients compared to S=O molecules (such as DMSO) resulting in similar or even lower LODs. The tradeoff for lower LODs, however, may be that an increased partition coefficient in a sorbent material is typically accompanied by a longer equilibration time for sorption and desorption.

Figure 9:
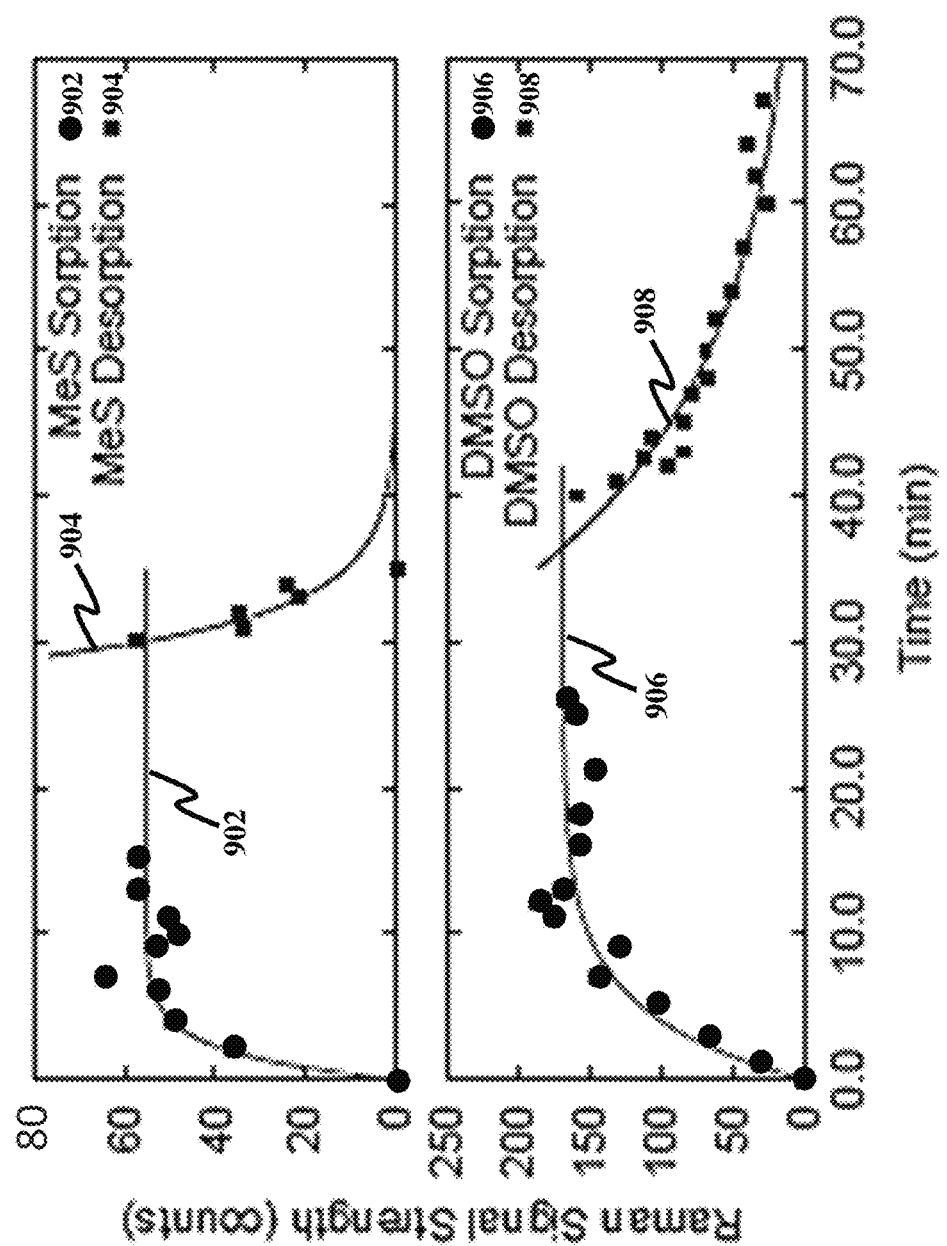
FIG. 9 are graphs illustrating Raman signal strength vs. time according to the embodiments herein.

FIG. 9, with reference to FIGS. 1 through 8, is a diagram illustrating the measured MeS sorption 902 and desorption 904, and DMSO sorption 906 and desorption 908, according to the embodiments herein. The data illustrated in FIG. 9 is acquired by taking a 20-second spectrum of a strongest Raman line for each MeS or DMSO analyte, and recording a spectrum every approximately 1-2 minutes during sorption and desorption. The sorption/desorption times for EA are too rapid (e.g., faster than the 20-second spectral collection interval) for this measurement technique to resolve.

In an exemplary embodiment, for waveguides 402 with a 1-2 μm polymer cladding, the sorption (desorption) times for MeS and DMSO are 1.8±0.4 min (3.1±0.6 min) and 8.8±0.4 min (14.5±1.5 min), respectively. The long measured desorption time in DMSO may be the result of incomplete purging of the DMSO vapor in a vapor generator used herein, and may not reflect the fundamental equilibrium time. It is noted that these equilibrium times depend on both the chemical species as well as the sorbent thickness. In an embodiment herein, heating of the sorbent may be used to further enhance desorption rates.

In gas sensing, using the evanescent field above silicon waveguides, analytes (e.g. methane molecules) may be detected at a single overtone resonance in the optical L-band. However, these techniques may be limited to molecules with multiple strong overtones in the NIR, and it is not clear how many molecules will have a number of strong enough overtones to perform trace-level detection and identification.

The embodiments herein provide for gas-phase NIR overtone absorption spectroscopy. Raman spectroscopy provides many narrow lines sufficient for chemical identification, for any analyte that is concentrated by a sorbent. Sorbents may be designed to target a class of analytes, such that a few sorbents could cover many different types of analytes, from organophosphonates to toxic chemicals to laboratory solvents and interferents.

Unlike Raman spectroscopy in hollow-core optical fibers, an embodiment herein provides a device 100 that is open on top, allowing for fast, simple exposure of trace analytes to the top of the waveguides, without the need for gas pumps or vacuum.

Raman spectroscopy of gas mixtures has conventionally been demonstrated in resonant optical cavities and multipass cells. However, because of the nature of the optics and the required (long) optical interaction lengths, these systems are fundamentally not compatible with miniaturization or chip-scale implementation. Conversely, the embodiments herein provide compatibility with miniaturization and chip-scale implementation.

Raman scattering on-chip from fluidic analytes using a waveguide-confined geometry is also conventionally used. However, this approach does not have the sensitivity to detect trace gases, since no sorbent is used. The embodiments herein overcome this problem by using a hypersorbent polymer to increase the density of the analyte and provide enhanced sensitivity to detect the analyte.

Chip-scale Raman spectroscopy of gases may be used without a waveguide-confined geometry. These approaches may use analytes confined on a chip using microfluidics. However, waveguide-confined Raman spectroscopy, as presented in the embodiments herein, is advantageous because of its inherent signal advantage over surface-normal Raman spectroscopy, and further since PIC manufacturing requires an approach that uses lightwaves that are fully guided on chip.

Figure 10:
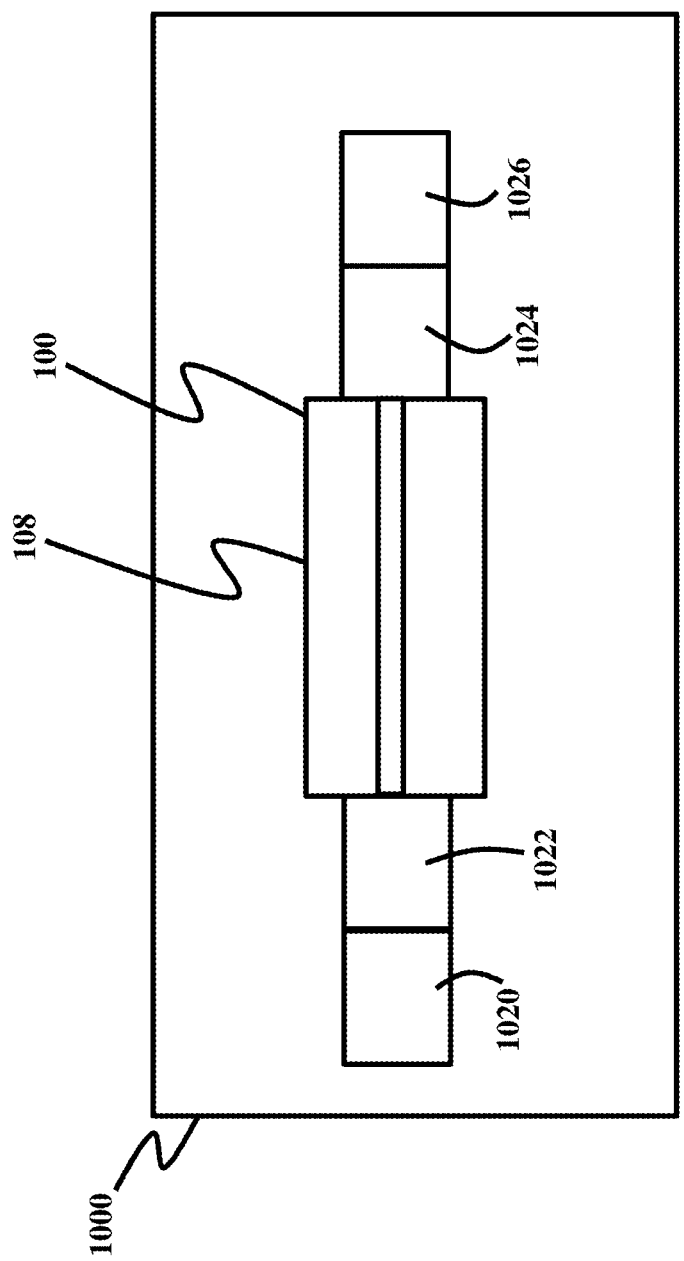
FIG. 10 is a schematic diagram illustrating a system according to an embodiment herein.

FIG. 10, with reference to FIGS. 1 through 9, is a schematic diagram illustrating a PIC 1000 according to an embodiment herein. In an embodiment, the PIC 1000 may include device 100, including the waveguide 108. The PIC 1000 may include any of the waveguide configurations and variations described herein. In an embodiment, a laser source 1020 may be implemented on the PIC 1000. The laser source 1020 may generate and transmit a laser radiation to a bandpass filter 1022. The band pass filter 1022 may filter the laser radiation generated by the source 1020 at a narrow-band frequency range, and couple the filtered narrow-band radiation to the waveguide 108. In an embodiment, the PIC 1000 includes a long-pass edge filter 1024 configured to block the laser radiation from an optical detector 1026. The Raman scattering signal is then used by the optical detector 1026 to identify the type of analyte.

Figure 11:
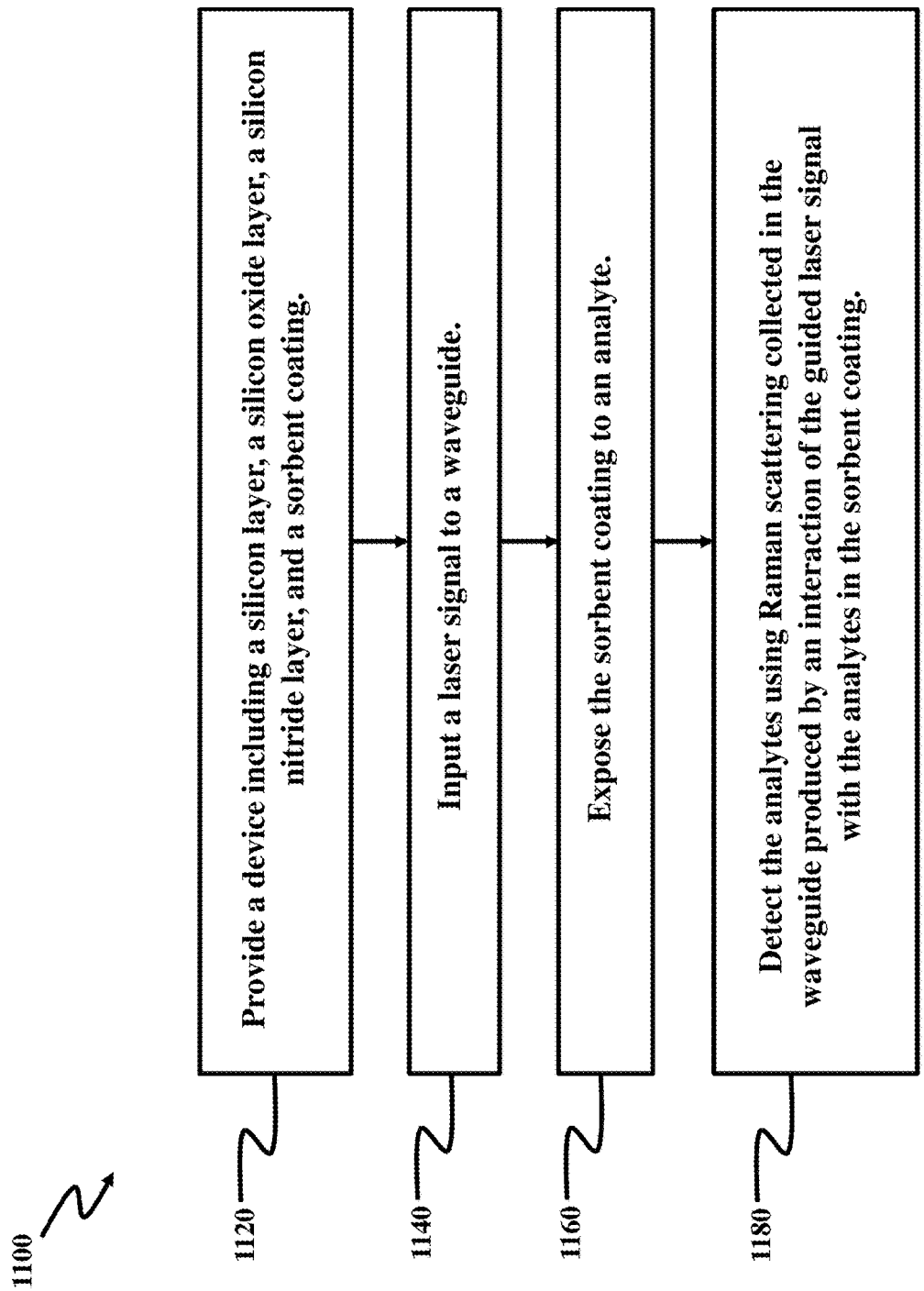
FIG. 11 is a flow diagram illustrating a method according to the embodiments herein.

FIG. 11, with reference to FIGS. 1 through 10, is a flow diagram illustrating a method 1100 for detecting an analyte, according to an embodiment herein. At step 1120, a device 100 is provided including a silicon layer 102, a silicon oxide layer 104 covering the silicon layer 102, and a silicon nitride layer 106 covering the silicon oxide layer 104. The silicon nitride layer 106 includes the waveguide 108. The waveguide 108 is covered by the sorbent coating 110 and is configured to absorb a portion of the analyte. Step 1140 involves inputting a laser signal to the waveguide 108. At step 1160 the sorbent coating 110 is exposed to the analyte. At step 1180, the analytes are detected using Raman scattering collected in the waveguide produced by an interaction of the guided laser signal with the analytes in the sorbent coating.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for detecting an analyte, said system comprising:
    a waveguide configured to receive a narrow-band laser signal; and
    a sorbent material covering an analyte detection region of said waveguide, wherein said sorbent material is configured to sorb said analyte and bring said analyte to an evanescent field of said waveguide, and wherein Raman scattering is produced by an interaction of said evanescent field and said analyte sorbed in said sorbent material along said analyte detection region of said waveguide, and
    said waveguide is further configured to collect said Raman scattering along said analyte detection region of said waveguide, wherein said collected Raman scattering indicates a type of said analyte, a flow cell, wherein said waveguide is located inside said flow cell, and wherein said flow cell comprises: a passage configured to allow a gas flow through said flow cell; and a first window and a second window, wherein the first and second windows are configured to allow light in and out of said flow cell, and a reflecting microscope objective that uses a Schwarzschild reflective objective, and is configured to: collect said Raman scattering transmitted by a second coupling component of said waveguide through said second window; and reduce chromatic dispersion in said collection of Raman scattering; and an off-axis parabolic mirror configured to couple said Raman scattering to said optical detector.

2. The system of claim 1, wherein said Raman scattering comprises back-scattered Raman scattering, and said system further comprises an optical detector configured to detect said back-scattered Raman scattering, which indicates said type of said analyte and propagates in an opposite direction as said narrow-band laser signal.

3. The system of claim 1, wherein said Raman scattering comprises forward-scattered Raman scattering, and said system further comprises an optical detector configured to detect forward-scattered Raman scattering, which indicates said type of said analyte and propagates in a same direction as said narrow-band laser signal.

4. The system f claim 3, further comprising:
    a pump laser source configured to generate a laser signal, said laser signal comprising said narrow-band laser signal;
    a band pass filter placed between said pump laser source and said waveguide, wherein said band pass filter is configured to filter said laser signal at frequencies of said narrow-band signal;
    an optic configured to focus said narrow-band signal on a first coupling component of
    said waveguide.

5. The system of claim 4, wherein said laser signal comprises any of 513 nm, 532 nm, 633 nm, 785 nm, 830 nm, 850 nm, and 980 nm wavelengths.

6. The system of claim 4, wherein said laser signal comprises any of a predominantly in-plane (quasi-transverse electric) polarization and an out-of-plane (quasi transverse magnetic) polarization.

7. The system of claim 1, wherein said optical detector comprises any of:
    a 300-groove/ram, 1.3 µm-blaze grating and a liquid nitrogen cooled, 1024 element InGaAs linear array detector, and
    a spectrograph configured to identify said analyte using wavelengths of said Raman scattering.

8. The system of claim 7, further comprising a long-pass edge filter placed between said waveguide and said optical detector, wherein said long-pass edge filter is configured to block said narrow-hand signal from said optical detector.

9. The system of claim 1, further comprising a detection device comprising:
    a substrate layer comprising a substrate material;
    a bottom cladding layer comprising a bottom cladding material, wherein said bottom cladding layer covers said substrate layer; and
    a core layer comprising a core material, wherein said core layer covers said bottom cladding layer, wherein said core material has a refractive index higher than said bottom cladding material, wherein said waveguide is patterned in said core layer, and wherein said bottom cladding material and said core material are transparent at frequencies of said narrow-band signal and said Raman scattering frequencies.

10. The system of claim 9, wherein said substrate material comprises silicon, said bottom cladding material comprises silicon oxide, and said core material comprises silicon nitride.

* * * * *